United States Patent [19]

Raines

[11] Patent Number: 5,147,333
[45] Date of Patent: Sep. 15, 1992

[54] NEEDLELESS INJECTION PORT WITH AUTOMATIC BACKCHECK VALVE

[75] Inventor: Kenneth Raines, Bethlehem, Pa.

[73] Assignee: Burron Medical Inc., Bethlehem, Pa.

[21] Appl. No.: 698,987

[22] Filed: May 13, 1991

[51] Int. Cl.⁵ .............................................. A61M 5/00
[52] U.S. Cl. ................................. 604/249; 604/256; 137/625.34; 251/149.6; 251/211
[58] Field of Search ................... 604/33, 82, 83, 246, 604/249, 256, 284, 247; 137/112, 625.4, 533, 614.19, 625.34; 251/149.1, 149.6, 149.7, 211

[56] References Cited

U.S. PATENT DOCUMENTS

| | | |
|---|---|---|
| 2,705,501 | 4/1955 | Fritzsch ............................ 137/112 |
| 2,756,740 | 7/1956 | Deane . |
| 3,416,567 | 2/1965 | Dardel et al. . |
| 3,572,375 | 3/1968 | Rosenberg . |
| 3,965,910 | 6/1976 | Fischer . |
| 4,063,555 | 12/1977 | Ulinder . |
| 4,496,348 | 1/1985 | Genese et al. . |
| 4,534,758 | 8/1985 | Akers et al. . |
| 4,745,950 | 5/1988 | Mathieu ............................ 604/33 |
| 4,819,684 | 4/1989 | Zaugg et al. . |
| 4,915,687 | 4/1990 | Sivert . |
| 5,006,114 | 4/1991 | Rogers et al. . |
| 5,049,128 | 10/1991 | Duquette ............................ 604/83 |

*Primary Examiner*—John D. Yasko
*Assistant Examiner*—Anthony M. Gutowski
*Attorney, Agent, or Firm*—Shoemaker and Mattare, Ltd.

[57] ABSTRACT

A needleless injection port and automatic backcheck valve comprises a generally tubular body having a pair of vertically offset ports extending laterally therefrom, and a spool within the bore for controlling communication between the ports. The spool is urged by a spring toward one end of the bore, which is open so that a syringe tip can be inserted to displace the spool from a position in which the ports communicate to a position in which they are isolated and secondary medication can be injected from the syringe.

4 Claims, 2 Drawing Sheets

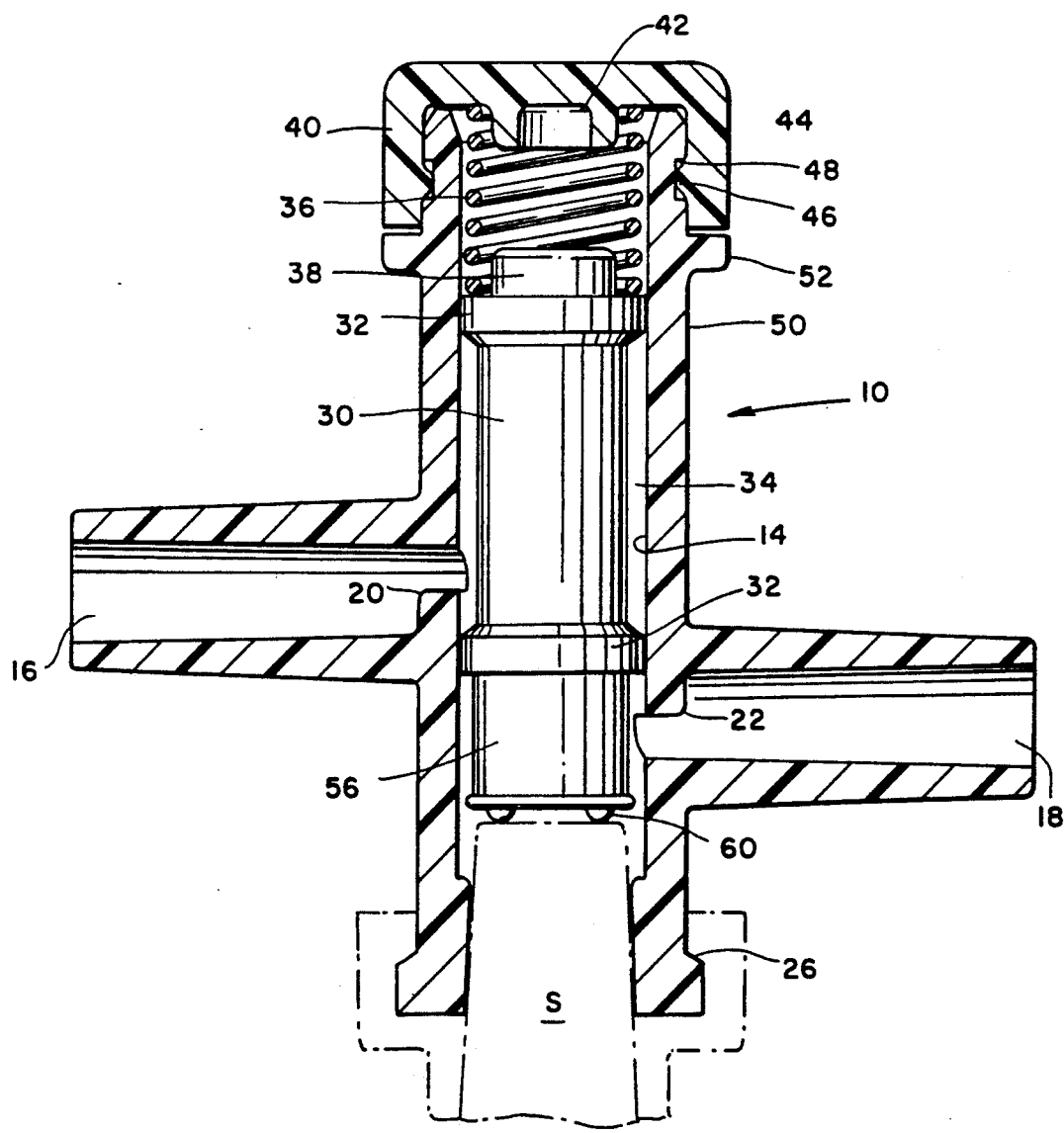

5,147,333

NEEDLELESS INJECTION PORT WITH AUTOMATIC BACKCHECK VALVE

BACKGROUND OF THE INVENTION

This invention relates to the art of fluid handling, particularly to a valve having three ports controlled by a spring-biased spool which is mechanically displaced by inserting a syringe tip into one of the ports.

When liquids are being administered to a patient from a I.V. bag or the like via a catheter, it may sometimes be desired to administer a secondary medication through the catheter. This can be done by providing the catheter conduit with an injection port, into which a syringe can be inserted. When materials are injected into the conduit from the syringe, however, they will naturally follow the path of least resistance, which in some cases may be toward the I.V. bag. It would therefore be possible to contaminate or taint the contents of the bag, if some means were not provided for preventing reverse flow. It is therefore customary to provide a check valve between the injection site and the bag.

Another consideration is that an injection port, if permanently installed in the catheter conduit, must not leak, or admit unintended materials.

SUMMARY OF THE INVENTION

It is an object of the invention to provide an injection port containing a simple valve, actuated by a syringe inserted into the port, which normally permits fluid to flow from an I.V. bag to a patient, but isolates the I.V. bag when secondary medication is injected through the port.

Another object is to provide a valve of simple design, which can be economically manufactured.

A further object is to enable one to provide a valve which can be disinfected with a sterilizing gas.

These and other objects are met by a needleless injection port and automatic backcheck valve comprising a generally tubular body having a pair of vertically offset ports extending laterally therefrom, and a spool within the bore for controlling communication between the ports. The spool is urged by a spring toward one end of the bore, which is open so that a syringe tip can be inserted to displace the spool from a position in which the ports communicate to a position in which they are isolated and secondary medication can be injected from the syringe.

BRIEF DESCRIPTION OF THE DRAWINGS

In the accompanying drawings,

FIG. 2 is a corresponding view, showing the spool in a raised position; and

DESCRIPTION OF THE PREFERRED EMBODIMENT

Figure 1:
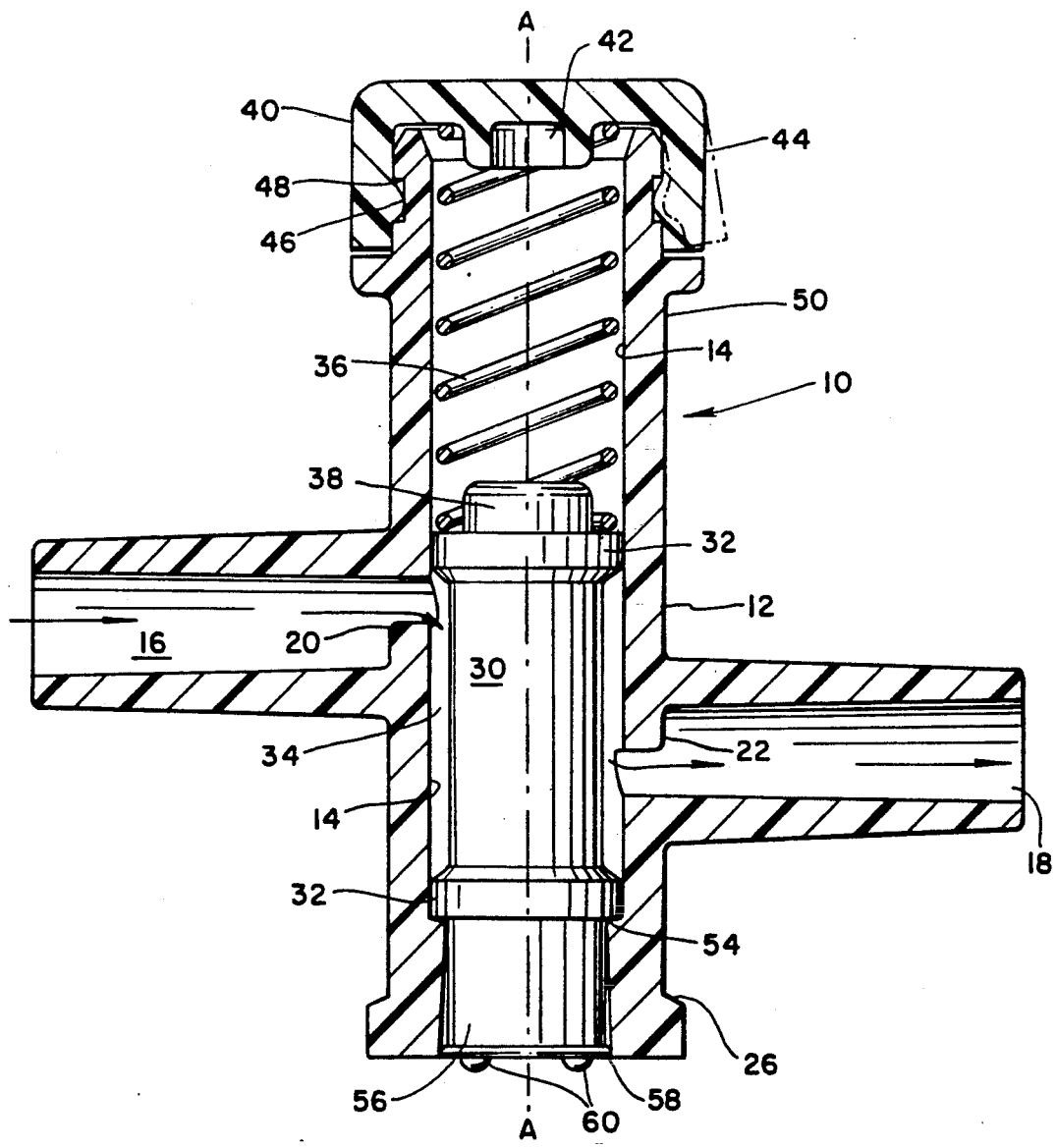
FIG. 1 is a sectional side elevation along a vertical plane of symmetry of a valve embodying the invention, showing the spool of the valve in its lowermost position.

As shown in FIGS. 1 and 2, a valve embodying the invention comprises a one-piece housing 10 injection molded from a plastic material, preferably a polycarbonate. The housing comprises a central, generally cylindrical body 12 having a bore 14 centered on an axis "A" which is vertically oriented in the drawing. The term "vertical" is used herein for clarity, to give meaning to directional terms such as "upper"; however, it should be understood that the valve may be used in any orientation.

An inlet 16 and an outlet 18 extend laterally from opposite sides of the body. The inlet and outlet are vertically offset so that they can be isolated by the spool valve described below. The effective height of each port is preferably reduced by a respective dam 20 or 22 molded into the body. These dams reduce the required travel of the spool, and thence the overall height of the valve.

The lower end of the body is provided with a luer fitting, comprising a short luer taper, whose diameter is less than that of the body bore, and a pair of lugs 26 forming a luer lock whereby a syringe ("S", FIG. 2) may be connected to the body.

The spool valve 30 confined within the bore 14 is formed from a thermoplastic elastomer material, or synthetic rubber, and has a solid cylindrical portion bounded by a pair of spaced rims 32, each fitting closely within the bore. The annular space between the rims is designated by reference numeral 34.

The spool is biased downward by a coil compression spring 36 bearing against the upper end of the spool, on which it is centered by a boss 38 that is formed integrally with the spool.

A cap 40 retains the spring 36 within the bore 14; the cap also has a centering boss 42 on its lower side. The downturned flange 44 is provided with an internal rib 46 that snaps into a circumferential groove 48 on the upper end of the central portion 12. The upper end 50 of the body is internally and externally chamfered to facilitate assembly. The protruding circumferential skirt 52 on the body, just below the cap flange, is aesthetic, and also, in conjunction with the rib and groove, helps prevent accidental or deliberate disassembly of the valve.

Figure 3:
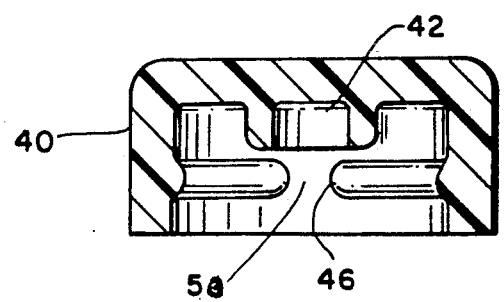
FIG. 3 is a sectional view of a component of the valve.

So that the valve can be sterilized by infusing a gas such as ethylene oxide, it is necessary that the cap not provide a hermetic seal with the body. For this reason, a vent is provided in the form of a cut-away portion 53 of the circumferential rib 46, as shown in FIG. 3. During a procedure in which the valve is first evacuated, then bathed in a sterilizing gas, the cap swells outward sufficiently (see broken lines in FIG. 1) to permit to gas the enter the space above the spool.

The luer taper, being smaller in diameter than the bore 14, forms a ledge 54 against which the lower rim of the spool normally rests (FIG. 1). Thus the ledge acts as a lower stop. Its upper edge is chamfered or rounded. In the position shown in FIG. 1, the lumens of the two lateral ports communicate through the annular volume defined between the spool rims.

The spool has a cylindrical extension 56 at its bottom end, below the lower flange, the diameter of the extension being sufficiently reduced to fit within the luer taper. A peripheral bead 58 around the lower end of the extension seats against the inner wall of the bore, and in that position acts as a seal. The bumps or protrusions 60 on the bottom, exposed surface of the spool prevent planar contact between that surface and the end of an inserted syringe tip, which could otherwise block the flow of liquid from the syringe.

The valve is assembled by inserting the spool into the central bore of the valve from above, then inserting the compression spring, and finally snapping the cap into place.

The valve may be assembled in an intravenous line, the left side port being connected to a gravity-fed container or bag, and the right side port being connected to tubing leading to a cannula or catheter. The valve normally permits substantially unrestricted flow from the infusion source to the patient, while the bead on the spool prevents leakage.

When it is desired to inject a fluid into the infusion line, the tip of a syringe is pushed against the exposed bottom surface of the spool. Upward pressure sufficient to overcome the spring bias, and the frictional force between the bead and the bore, moves the spool upward to the position shown in FIG. 2, wherein the lower rim seals off the passage between the two ports. Now, any fluid injected into the bottom of the valve flows into the patient tube. When the syringe is removed, the valve returns to its initial position.

Inasmuch as the invention is subject to modifications and variations, it is intended that the foregoing description and the accompanying drawings shall be interpreted as illustrative of only one form of the invention, whose scope is to be measured by the following claims.

I claim:

1. A needleless injection port and automatic back-check valve comprising
    a generally tubular body having a bore extending along a first axis,
    a pair of ports extending laterally from said body, each port being in communication with said bore, and said ports being offset along said axis,
    a spool inserted within said bore, said spool having a pair of rims defining an annular space therebetween,
    means for biasing said spool toward one end of said bore,
    said spool being axially movable between a first position in which said ports are in fluid communication with one another via said annular space, and a second position in which one of said rims blocks such communication,
    one end of the body having an opening into which a syringe tip can be inserted to move said spool from said first position to said second position, whereupon the syringe is in fluid communication with only one of said ports,
    wherein said body has a luer fitting at one end for receiving a syringe, the fitting including a luer taper of lesser diameter than said bore, thus defining a circumferential ledge at one end of the bore which provides a stop for the spool, and
    the spool has a cylindrical extension at one end, said extension fitting closely within said luer taper, and having a bead at its distal end which bears against the luer taper, forming a seal therewith.

2. A needleless injection port and automatic back-check valve comprising
    a generally tubular body having a bore extending along a first axis,
    a pair of ports extending laterally from said body, each port being in communication with said bore, and said ports being offset along said axis,
    a spool inserted within said bore, said spool having a pair of rims defining an annular space therebetween,
    said spool being axially movable between a first position in which said ports are in fluid communication with one another via said annular space, and a second position in which one of said rims blocks such communication,
    one end of the body having an opening into which a syringe tip can be inserted to move said spool from said first position to said second position, whereupon the syringe is in fluid communication with only one of said ports,
    a coil compression spring bearing against the end of the spool opposite the end adjacent the opening, for biasing the spool toward the opening, and
    a cap for retaining the spring within the bore,
    said cap having a downturned flange which fits over one end of the body, the body having a circumferential groove thereon, and said flange having a corresponding internal circumferential rib which snaps into the groove when the valve is assembled.

3. The invention of claim 2, wherein the circumferential rib extends over less than the entire circumference of the flange, providing a gap through which sterilizing gas may enter the valve.

4. A needleless injection port and automatic back-check valve comprising
    a generally tubular body having a bore extending along a first axis,
    a pair of ports extending laterally from said body, each port being in communication with said bore, and said ports being offset along said axis,
    a spool inserted within said bore, said spool having a pair of rims defining an annular space therebetween,
    means for biasing said spool toward one end of said bore,
    said spool being axially movable between a first position in which said ports are in fluid communication with one another via said annular space, and a second position in which one of said rims blocks such communication,
    one end of the body having an opening into which a syringe tip can be inserted to move said spool from said first position to said second position, whereupon the syringe is in fluid communication with only one of said ports,
    wherein each of said ports intersects said bore at an opening which is partially obstructed by a dam, to reduce the required stroke of the spool.

* * * * *